United States Patent [19]
Orning et al.

[11] Patent Number: 5,962,408
[45] Date of Patent: Oct. 5, 1999

[54] DISULPHIDE-CYCLO-[H-CYS-GLU-GLN-TYR-CYS-OH], AND ITS USE IN BLOOD-CLOTTING DISORDERS

[75] Inventors: Lars Orning; Kjell Steinar Sakariassen; Kjell Eric Agner; Peter Fischer, all of Oslo; May Engebretsen, Jar, all of Norway

[73] Assignee: Nycomed Imaging AS, Norway

[21] Appl. No.: 08/849,249

[22] PCT Filed: Dec. 15, 1995

[86] PCT No.: PCT/GB95/02945

§ 371 Date: Sep. 10, 1997

§ 102(e) Date: Sep. 10, 1997

[87] PCT Pub. No.: WO96/18653

PCT Pub. Date: Jun. 20, 1996

[30] Foreign Application Priority Data

Dec. 15, 1994 [GB] United Kingdom .................. 9425380

[51] Int. Cl.⁶ .......................... A61K 38/00; A61K 38/12; C07K 5/00; C07K 7/00
[52] U.S. Cl. ................................. 514/11; 514/9; 530/317
[58] Field of Search ................................ 530/317; 514/9, 514/11

[56] References Cited

FOREIGN PATENT DOCUMENTS 90 03390  4/1990  WIPO .
95 00541  1/1995  WIPO .

*Primary Examiner*—Avis M. Davenport
*Attorney, Agent, or Firm*—Bacon & Thomas

[57] ABSTRACT

The present invention relates to disulphide-cyclo-[H-Cys-Glu-Gln-Tyr-Cys-OH] and salts thereof which are useful in the treatment of blood clotting disorders.

5 Claims, 2 Drawing Sheets

DISULPHIDE-CYCLO-[H-CYS-GLU-GLN-TYR-CYS-OH], AND ITS USE IN BLOOD-CLOTTING DISORDERS

CROSS-REFERENCE TO RELATED APPLICATIONS

This application is a 371 of PCT/GB95/02945 filed Dec. 15, 1995.

BACKGROUND OF THE INVENTION

1. Field of the Invention

The present invention is concerned with peptide reagents and compositions thereof which reduce blood clot formation.

2. Description of the Related Art

Blood clotting relies upon a series or cascade of activating reactions to produce the ultimate fibrin clot. The cascade leading to fibrin formation may be triggered initially in two different ways—by contact with abnormal surfaces (the "intrinsic pathway") or by traumatization of blood vessels which causes secretion of the lipoprotein known as "tissue factor" or TF (the "extrinsic pathway"). The present invention is primarily concerned with the extrinsic blood clotting pathway.

TF is an integral membrane protein which appears on many cell types. However, cells which constitutively express TF, for example the muscle cells of vessels intima, are not normally exposed to blood (see Edgington et al., Thromb. Haemostas. 66(1): 67–69 (1991)). Thus initiation of the extrinsic blood clotting pathway appears to require either the disruption of blood vessel walls (see Almus et al., Blood 76: 354–360 (1990)) and/or activation of endothelial cells or monocytes to express TF (see Edwards et al., Blood 54: 359–370 (1979) and Bevilaqua et al., PNAS USA 83: 4533–4537 (1986)). Disruption of the blood vessel wall may occur due to fissuring of an atherosclerotic plaque which exposes tissue macrophages and smooth muscle cells to the blood (see Wilcox et al., PNAS USA 86: 2839–2843 (1989)). TF may also be exposed following injury to blood vessels during thrombolytic therapy, surgery for grafting, mechanical restoration of vessel patency or other similar techniques. On the other hand, TF expression in endothelial cells or in monocytes may be induced during sepsis due to production of tumour necrosis factor-α or interleukin-1 (see Edwards et al., supra and Gregory et al., J. Clin. Invest. 76: 2440–2445 (1985)).

The serine protease Factor VIIa (FVIIa) is involved in the extrinsic blood clotting pathway. FVIIa is formed by proteolysis from its inactive pro-enzyme Factor VII (FVII) by other participants in the blood clotting process, including Factor Xa, Factor XIIa, Factor IXa or thrombin. Activation of FVII to FVIIa has been reported to be markedly enhanced when FVII is bound to its co-factor tissue factor (TF) (see Nemerson, Semin. Hematol. 29(3): 170–176 (1992)). Yamamoto et al. have also suggested that conversion of FVII to FVIIa may be autocatalytic (see J. Biol. Chem. 267(27): 19089–19094 (1992)).

FVIIa forms a complex with TF in the presence of calcium ions and the FVIIa/TF complex catalyses the conversion of Factor X to its active form, Factor Xa, in the next step of the blood clotting process via the extrinsic pathway.

The structure of FVII has been investigated and the cDNA sequence was reported by Hagen et al. in PNAS USA 83: 2412–2416 (1986). FVII is a vitamin K dependent protein and, by analogy to other vitamin K dependent proteins, a putative γ-carboxyglutamic acid (Gla) domain has been identified at the amino terminal. It was predicted, again by analogy to the other vitamin K dependent proteins, that the Gla domain was required for binding to TF (see Hagen et al., supra). The Gla domain is followed by two potential growth factor (GF) domains.

However, the literature has not suggested any function for the GF domains.

Activation of the extrinsic pathway for blood clot formation has been suggested as the primary event leading to fibrin formation (see Weiss et al., Blood 71: 629–635 (1988) and Weiss et al., Blood 73: 968–975 (1989)) and is thus of prime importance in the pathogenesis of arteriosclerotic lesions and in reocculusion and and restenosis following endarterectomy. However effective therapeutic agents able to intervene in the activation of this pathway are not available, despite demand (see Shepard, TIBTECH 9: 80–85 (1991)).

The present invention provides a novel peptide and analogues or salts thereof which inhibit the association of FVII or FVIIa with TF. Through the action of the peptides according to the invention, formation of the FVIIa/TF complex is limited and therefore activation of Factor X is reduced.

Certain peptides stated to be useful in blood clotting therapy are disclosed in WO-A-91/07432 of the Board of Regents, The University of Texas System. The peptides disclosed either occur in the region between the Gla and the first GF domain or in the catalytic domain of FVII or FVIIa. Although inhibition of FVIIa/TF complex formation is discussed, those peptides disclosed in WO-A-91/07432 which cause such an effect do so via inhibition of the Gla function. Such peptides are thus unspecific in their action since other physiological proteins have Gla domains, for example protein C which has close sequence homology to the Gla domain of FVII. Hence, the function of protein C would also be disturbed by peptides disclosed in WO-A-91/07432 in an undesirable way.

In WO-A-90/03390, Corvas Inc. suggest that certain peptides derived from the amino acid sequence of FVII (or FVIIa) might be useful in preventing the action of the fully formed FVIIa/TF complex. Two particular peptide sequences were disclosed in WO-A-90/03390 as being active in this respect. The sequence -VGHFGV- is based upon amino acids nos. 372–377 of FVII which are situated near the carboxy terminus. The other sequence is -SDHTGTKRSCR- which is located at amino acids nos. 103–113 of FVII and is part of the second GF domain. Corvas Inc indicate that these peptides, and analogues thereof, inhibit the cascade reaction initiated by the FVIIa/TF complex.

Furthermore, in Table 1, on page 14 of WO90/03390, it is indicated that of the various regions of the second GF domain, only SDHTGTKRSC (103 to 112) was active and that the other regions, namely from amino acids 50 to 101 and 114 to 127, were totally inactive in inhibition of activation of Factor X by Factor VII and tissue factor.

However, we have shown that, contrary to the reported findings of Corvas Inc., the region SDHTGTKRSC from 103 to 112 is a rather poor inhibitor of the binding of Factor VII to tissue factor and that certain of the regions said to be inactive are, in fact, highly active.

Our co-pending International application PCT/GB94/01315 discloses peptide fragments from the region 91 to 104 of the Factor VII sequence which are particularly active as inhibitors of the binding of Factor VII to tissue factor (TF) and comparative results are provided for several of these as compared with fragments from neighbouring regions, including the above fragment of Corvas Inc. Although a Table was provided which identified fragments which had been made, two of the Figures included results for a compound identified as 98–102(C) which was not in the Table. The reference (C) meant that the compound, which has the amino acid sequence CEQYC (Cys-Glu-Gln-Tyr-Cys), was in a cyclic form in which the two C (cysteine) residues were joined by a disulphide bond. Although not stated, the result indicated by the Figure was that for a derivative in cyclic form having an N-terminal acetyl group and a C-terminal carboxamide group, namely, disulphide-cyclo-[Ac-Cys-Glu-Gln-Tyr-Cys-NH$_2$]. On the other hand, the Table included a fragment identified as "98–102" which was, however, indicated to be AEQYV, an analogue of CEQYC in which the terminal cysteine residues were replaced by alanine and valine, and was thus not capable of forming a cyclic derivative. The inhibition of binding of Factor VII to tissue factor reported for the so-called 98–102(C) was negligible.

BRIEF SUMMARY OF THE INVENTION

We have now found that the compound disulphide-cyclo-[H-Cys-Glu-Gln-Tyr-Cys-OH] having free terminal NH$_2$ and COOH groups is outstandingly superior to any of the fragments disclosed in our above International application.

According to the present invention therefore we provide the peptide disulphide-cyclo-[H-Cys-Glu-Gln-Tyr-Cys-OH] and salts thereof.

Figure 1:
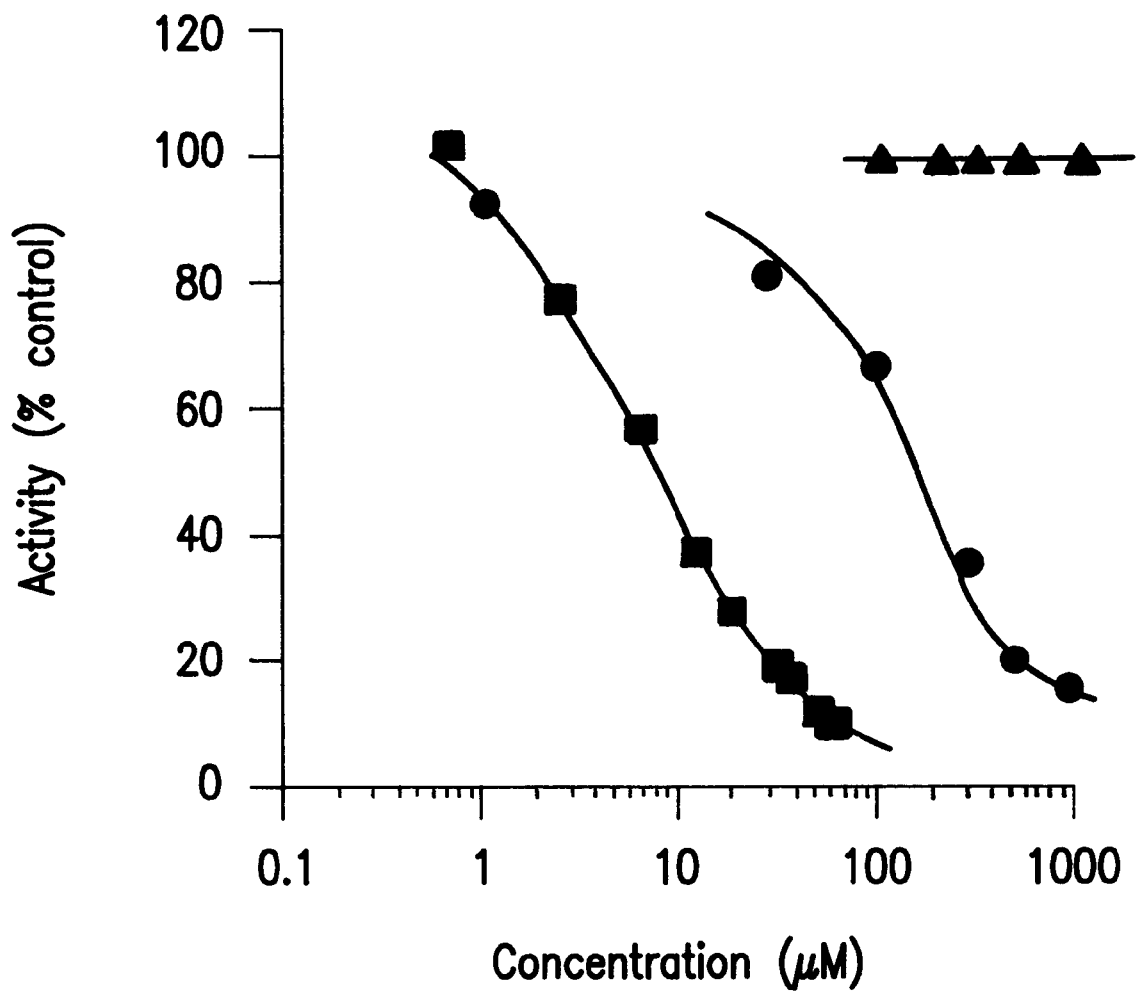
FIG. 1 illustrates representative experimental dose-inhibition data.
Figure 2A:
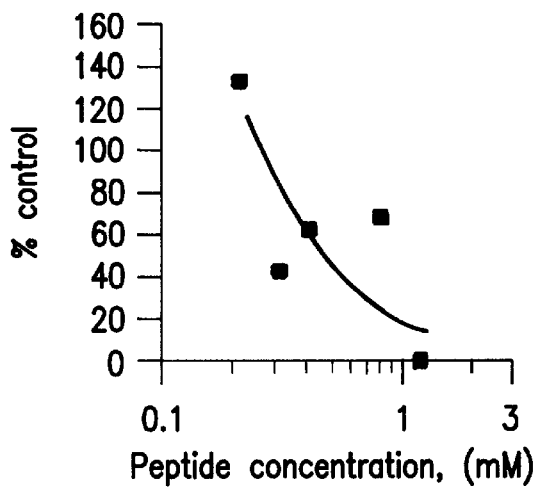
FIG. 2 summarizes assay results.
Figure 2B:
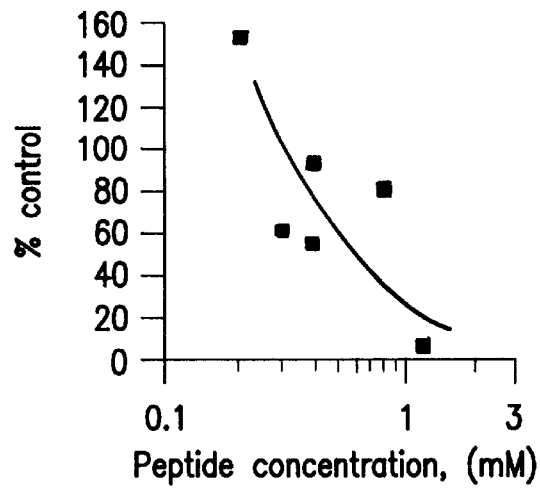
Figure 2C:
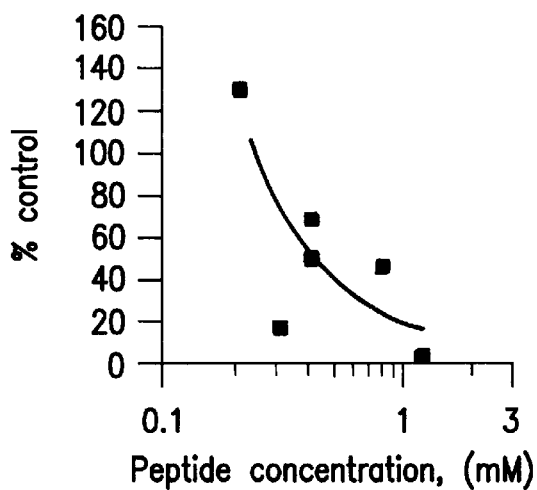
Figure 2D:
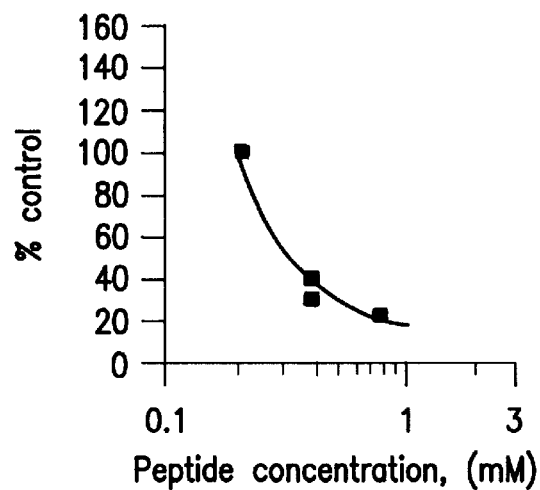

The new cyclic peptide (hereinafter designated disulphide-cyclo-[H-Cys-Glu-Gln-Tyr-Cys-OH], apart from exhibiting superior solubility properties in physiological media compared to the previously disclosed peptide disulphide-cyclo-[Ac-Cys-Glu-Gln-Tyr-Cys-NH$_2$], is distinguished by its high inhibitory action against binding of FVII with TF and can be characterised by having an IC$_{50}$ in the two-stage chromogenic assay of A. Kumar et al. (J. Biol. Chem. 266. 915–921, 1991) of 0.01 mM. The end-capped peptide disulphide-cyclo-[Ac-Cys-Glu-Gln-Tyr-Cys-NH$_2$] referred to above had an IC$_{50}$ of approximately 0.2 mM under similar assay conditions.

Apart from the ability of the peptide disulphide-cyclo-[H-Cys-Glu-Gln-Tyr-Cys-OH] to inhibit the complex formation between FVIIa and TF in various biochemical assays, we have also found this peptide to be efficacious in a clinically relevant ex vivo model of TF/FVII-dependent arterial human thrombogenesis. Using the methods and apparatus described in K.S. Sakariassen et al. (1990, Arteriosclerosis, 10, 276) and continuous infusion with homogeneous mixing of peptide solution into the blood stream proximal to the thrombogenic surface, we observe essentially complete inhibition of thrombus formation at final peptide concentrations of around 1 mM.

According to a further aspect of the invention we provide the use of the compound disulphide-cyclo-[H-Cys-Glu-Gln-Tyr-Cys-OH] and/or a salt thereof for the preparation of pharmaceutical compositions for prevention or inhibition of binding of tissue factor to FVII.

Salts of the cyclic peptide of the invention include physiologically acceptable salts such as acid addition salts for example the hydrochloride.

In certain of the sequences referred to above, the standard one letter code is used to refer to each naturally occuring amino acid. This code is standard nomenclature within the art and can be found in any standard biochemical textbook such as "Biochemistry" Stryer, published by W.H. Freeman and Company. Similarly, where the three-letter code is used, this has its normal meaning as set out in the above textbook of Stryer. In each case the amino residues, apart from glycine, are in the L-form.

The present invention also provides a pharmaceutical composition comprising disulphide-cyclo-[H-Cys-Glu-Gln-Tyr-Cys-OH] and/or salts thereof. The peptides may be administered together with any physiologically acceptable excipient known to those skilled in the art, Examples of suitable excipients include water and oil.

The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, powders, capsules or sustained release forms. Conventional pharmaceutical excipients as-well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1–10 mg, for example 1–5 mg of the peptide of formula (I) or salt thereof.

As indicated above, one aspect of the invention provides the compound disulphide-cyclo-[H-Cys-Glu-Gln-Tyr-Cys-OH] and salts thereof for use in the treatment or prevention of blood clotting disorders or problems. Blood clotting disorders include thrombosis (particularly vascular thrombosis or deep vein thrombosis), acute myocardial infarction, restenosis, reclosure, angina, cerebrovascular disease, peripheral arterial occlusive disease, hypercoagulability and pulmonary embolism. The peptides according to the invention can also be used to prevent occurrence of blood clotting problems caused by, for example, injury to blood vessels during thrombolytic therapy, grafting surgery, vessel patency restoration etc. Blood clotting disorders may be triggered by sepsis due to production of TNF-α or IL-1.

In a still further aspect, the present invention also provides a method of treatment of blood disorders in the mammalian, preferably human, animal body, said method comprising administering to said body the compound disulphide-cyclo-[H-Cys-Glu-Gln-Tyr-Cys-OH] or a salt thereof. Prophylactic methods of treatment are also provided, whereby a peptide according to the invention is administered to a patient to prevent or reduce the occurrence of possible blood clotting problems, for example during surgery or other invasive techniques. The peptide will of course normally be administered in the form of a pharmaceutically acceptable composition.

The peptide of the invention may be synthesised in any convenient way. Generally the reactive groups present (for example amino, thiol and/or carboxyl) will be protected during overall synthesis. The final step in the synthesis will normally be cyclisation, generally following the deprotection of a protected derivative of the peptide of the invention.

Alternatively, protected (including solid phase-bound) peptides may be cyclised through disulphide bond formation prior to deprotection (resin detachment) (cf. F. Albericio et al., 1991, Int. J. Peptide Protein Res, 37, 402–413).

In another aspect therefore, the present invention provides a process for the preparation of the cyclic peptide disulphide-cyclo-[H-Cys-Glu-Gln-Tyr-Cys-OH] and/or salts thereof by cyclisation of a corresponding linear peptide.

In general, the cyclisation may be effected using oxidation, eg. with oxygen at high dilution under basic conditions, or eg. under acidic conditions in trifluoroacetic acid with dimethylsulphoxide. If the Cys residues are protected by S-trityl or S-acetamidomethyl groups, deprotection and oxidation can be effected simultaneously using iodine or thallium (III) trifluoroacetate.

In a preferred method of synthesis, the Cys residues are separately protected, one with an acid labile group such as trityl and one with an acid stable disulphide-forming protecting group such as the 3-nitro-2-pyridylsulphenyl group (Npys). If the peptide is assembled using acid labile protecting groups and, where a solid support is used, an acid labile ester linkage, conventional acidolysis (eg. using the phenol/ethandithiol/thioanisole/TFA/water acidolysis mixture of D. S. King et al. 1990, Int. J. Peptide Protein Res., 36, 255-256) will provide the peptide in linear form which is fully deprotected apart from the Npys group. Under basic conditions eg. 0.1M aqueous ammonium bicarbonate at pH 9.0, the peptide undergoes intramolecular disulphide exchange to yield the desired cyclic product.

In building up the peptide chains, one can in principle, start either at the C-terminal or the N-terminal although only the C-terminal starting procedure is in common use.

Thus, one can start at the C-terminal by reaction of a suitably protected derivative of, for example tyrosine with a suitably protected derivative of cysteine. The cysteine derivative will have a free α-amino group while the tyrosine will have either a free or activated carboxyl group and a protected amino group. After coupling, the intermediate may be purified, for example by chromatography, and then selectively N-deprotected to permit addition of a further amino acid residue. This procedure is continued until the required amino acid sequence is completed.

Carboxylic acid activating substituents which may, for example, be employed include symmetrical or mixed anhydrides, or activated esters such as for example the p-nitrophenyl ester, 2,4,5-trichlorophenyl ester, N-hydroxybenzotriazole ester (OBt), or N-hydroxysuccinimidyl ester (OSu).

Amino components may be acylated directly by amino acid derivatives possessing a free carboxyl group with the aid of coupling reagents such as 2-(1H-benzotriazole-1-yl)-1,1,3,3-tetramethyluronium hexafluorophosphate and other reactive species derived from benzotriazole, as well as carbodiimides, 2-ethoxy-1-ethoxycarbonyl-1,2-dihydroquinoline, etc. Often catalysts which also possess racemisation-suppressing properties are added to the acylation mixtures, eg. 1-hydroxybenzotriazole.

In general it is convenient to effect the coupling reactions at low temperatures, for example, −20° C. up to ambient temperature, conveniently in a suitable solvent system, for example, tetrahydrofuran, dioxan, dimethylformamide, methylene chloride or a mixture of these solvents.

It may be more convenient to carry out the synthesis on a solid phase resin support. Chloromethylated polystyrene (cross-linked with 1% divinyl benzene) is one useful type of support; in this case the synthesis will start at the C-terminal, for example by coupling N-protected cysteine to the support.

A preferred support is p-alkoxybenzylalcohol resin (S-S, Wang, J. Am Chem. Soc. 1973, 95: 1328–1333) which cleaves by acidolysis to provide the free peptide in carboxyl form. 4-Hydroxymethylphenylacetamidomethyl (PAM) resins may also be used to provide the peptide in carboxyl form (B. Gutte, R. B. Merrifield (1971), J. Biol. Chem. 246, 1922; A. R. Mitchell et al. (1978) J. Am. Chem. Soc. 98, 7357.)

A wide choice of protecting groups for amino- acids are known and are exemplified in Schröder, E., and Lübke, K., The Peptides, Vols. 1 and 2, Academic Press, New York and London, 1965 and 1966; Pettit, G. R., Synthetic Peptides, Vols. 1–4, Van Nostrand, Reinhold, New York 1970, 1971, 1975 and 1976; Houben-Weyl, Methoden der Organischen Chemie, Synthese von Peptiden, Band 15, Georg Thieme Verlag, Stuttgart 1974; Amino Acids, Peptides and Proteins, Vol.4–8, The Chemical Society, London 1972, 1974, 1975 and 1976; Peptides, Synthesis-physical data 1–6, Wolfgang Voelter, Eric Schmidt-Siegman, Georg Thieme Verlage Stuttgart, N.Y., 1983; The Peptides, Analysis, synthesis, biology 1–7, Ed: Erhard Gross, Johannes Meienhofer, Academic Press, N.Y., Sari Fransisco, London; Solid phase peptide synthesis 2nd ed., John M. Stewart, Janis D. Young, Pierce Chemical Company.

Thus, for example amine protecting groups which may be employed include protecting groups such as carbobenzoxy (hereinafter also designated Z) t-butoxycarbonyl (hereinafter also designated Boc) and 9-fluorenylmethoxycarbonyl (hereinafter also designated Fmoc). It will be appreciated that when the peptide is built up from the C-terminal end, an amine-protecting group will be present on the α-amino group of each new residue added and will need to be removed selectively prior to the next coupling step. One particularly useful group for such temporary amine protection is the Fmoc group which can be removed selectively by treatment with piperidine in an organic solvent.

Carboxyl protecting groups which may, for example be employed include readily cleaved ester groups such as benzyl (Bzl), p-nitrobenzyl (ONb), or t-butyl (OtBu) groups as well as the linkers on solid supports, for example p-alkoxy benzyl alcohol groups linked to polystyrene.

Thiol protecting groups include p-methoxybenzyl (Mob), trityl (Trt), acetamidomethyl (Acm) and 3-nitro-2-pyridylsulphenyl (Npys).

It will be appreciated that a wide range of other such groups exists as, for example, detailed in the above-mentioned literature references, and the use of all such groups in the hereinbefore described processes fall within the scope of the present invention.

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoro acetic acid.

The following Examples are given by way of illustration only.

EXAMPLE 1

Synthesis of disulphide-cyclo-[H-Cys-Glu-Gln-Tyr-Cy-OH]

Solid-phase peptide synthesis

The peptide was assembled using an Applied Biosystems model 433A peptide synthesiser with standard 0.1 mmol FastMoc cycles (acylations with 10-fold molar excess of Fmoc-amino acids and 2-(1H-benzotriazole-l-yl)-1,1,3,3-tetramethyluronium hexafluorophosphate/1-hydroxybenzotrazole/$Pr^i_2NEt$ in N-methyl-pyrrolidone). Fmoc-Cys(Trt)-[p-alkoxybenzyl alcohol resin (0.55 mmol/g functionality; 0.1 mmol; cf.: S.-S. Wang, J. Am. Chem. Soc., 1973, 95: 1328–1333) was deprotected with piperidine/DMF and acylated with Fmoc-Tyr($Bu^t$)—OH. Further elongation was carried out similarly with Fmoc-Gln(Trt)—OH, Fmoc-Glu(OBu$^t$)—OH and Boc-Cys(Npys)—OH. The complete peptidyl resin was further washed with $CH_2Cl_2$ and $Et_2O$ and was dried in vacuo (296 mg dry weight). This material was treated with a mixture containing 0.75 g PhOH, 0.25 mL 1,2-ethanedithiol, 0.5 mL PhSMe, 0.5 mL $H_2O$ and 10 mL $CF_3COOH$ for 1 hour with agitation of the reaction vessel. Resin residue was then removed by filtration and washing with small aliquots of neat $CF_3COOH$. The combined filtrate and washings were concentrated by rotary evaporation. The crude peptide was precipitated by addition of $Et_2O$. The precipitate was collected by filtration and washing with $Et_2O$ until the washings were practically colourless. The peptide was then dried, resuspended in 0.1% aq $CF_3COOH$ and lyophilised. A yellow powder containing H-Cys(Npys)-Glu-Gln-Tyr-Cys-OH (62.2 mg, ca. 78% relative to original resin loading) was thus obtained.

Cyclisation and Purification.

This material was dissolved 0.1 M aqueous $NH_4HCO_3$ (5 mL) and the resulting yellow solution was adjusted to pH=9 by addition of 0.4 mL of 1 M aqueous $NH_4HCO_3$. The mixture was stirred and after a total reaction time of 2.5 hours (monitoring by analytical RP-HPLC), the now colourless solution was injected (two runs) directly onto a preparative RP-HPLC column (Vydac 218TP1022, 22×250 mm) which was then eluted at 10 mL/min with a gradient of 2 to 6% MeCN in 0.1% aq $CF_3COOH$ over 60 minutes. The eluant was monitored at 280 nm and fractions of 1 minute were collected. Those fractions which were pure by analytical RP-HPLC (Vydac 218TP54, 4.6×250 mm; 1 mL/min, 0–12% MeCN in 0.1% aq $CF_3COOH$ over 20 minutes, $\lambda=215$) were pooled and lyophilised to yield 26.7 mg of pure ($t_R$=16.7 min; >99% by HPLC) cyclic H-Cys-Glu-Gln-Tyr-Cys-OH peptide. MALDI-TOF MS $[M+H]^+$=644.1, $C_{25}H_{34}N_6O_{10}S_2$=642.7. FAB-MS: $[M+H]^+$=643.3. Amino acid analysis: Glx, requires 2 (1 Glu & 1 Gln), found 2.01); Cys, requires 2, found 1.99 (determined as cysteic acid); Tyr, requires 1, found 1.00.

Reduction.

An aliquot of pure peptide (0.1 mg) was dissolved in 0.1 mL of 1 M aqueous $NaHCO_3$ and dithiothreitol (1 μL of a 1 M aqueous solution) was added. After short incubation an aliquot of the solution was analysed by RP-HPLC (conditions as above); this showed quantitative conversion to the reduced H-Cys-Glu-Gln-Tyr-Cys-OH form ($t_R$=21.2 min).

EXAMPLE 2

Inhibition of factor VIIa/tissue factor-catalysed factor X activation by disulphide-cyclo- [H-Cys-Glu-Gln-Tyr-Cys-OH]

This was determined using a two-stage chromogenic biochemical in vitro assay, essentially as described (A. Kumar et al., 1991, J. Biol. Chem., 266, 915). In short: peptides were pre-incubated with lipidated TF (5 pM; from American Diagnostica, Inc., Greenwich, Conn., USA) and calcium (5 mM) for 10 minutes prior to addition of FVIIa (5 pM; from Novo Nordisk A/S, Gentofte, Denmark) and FX (20 nM; from Enzyme Research Laboratory, South Bend, Ind., USA). Reactions were terminated by addition of EDTA (50 mM) and formation of FXa was monitored using the chromogenic FXa substrate S2765 (0.4 mM; from Chromogenix, Möndal, Sweden) and measuring the absorbance increase at 405 nm in a microtitre plate reader. The concentration for half-maximal inhibition ($IC_{50}$) was determined from dose-inhibition curves.

In this assay the peptide disulphide-cyclo-[H-Cys-Glu-Gln-Tyr-Cys-OH] exhibited an $IC_{50}$ value of 10.1±5.0 μM (mean±standard deviation). The corresponding end-capped peptide disulphide-cyclo-[Ac-Cys-Glu-Gln-Tyr-Cys-$NH_2$], disclosed previously in PCT/GB94/01315, exhibited 26-fold lower potency in the same assay, i.e. an $IC_{50}$ value of 265±174 μM. Representative experimental dose-inhibition data are presented in FIG. 1 (Legend: ■, disulphide-cyclo-[H-Cys-Glu-Gln-Tyr-Cys-OH]; ●, disulphide-cyclo-[Ac-Cys-Glu-Gln-Tyr-Cys-$NH_2$]; ▲, negative control peptide), where the results are expressed as percent FXa formation relative to untreated control.

EXAMPLE 3

Effect on tissue factor-dependent plasma coagulation of disulphide-cyclo-[H-Cys-S-Glu-Gln-Tyr-Cys-OH]

A one-stage in vitro coagulation assay was used as follows: peptides dissolved in 3-[N-morpholino]propane-sulphonic acid buffer (100 mM, pH 7.4) and NaCl (100 mM) were premixed with diluted (1:50 in saline) lipidated TF (Thromborel S®, Behringwerke AG, Marburg, Germany) and $CaCl_2$ (5 mM final concentration) and the solutions were kept at 37° C. for 2 minutes. The coagulation reaction was initiated by addition of a thawed aliquot of frozen platelet-free human plasma pool (37° C.). The clotting-time for four replicate incubations were simultaneously determined automatically in an electromagnetic coagulometer (Thrombotrack 4, Nycomed Pharma AS, Oslo, Norway). The mean value for the clotting times determined from the replicate samples were converted to arbitrary TF units by a log-log calibration curve generated with Thromborel.

A dose-dependent prolongation of the clotting time was observed with the peptide disulphide-cyclo-[H-Cys-Glu-Gln-Tyr-Cys-OH]. The concentration for half-maximal inhibition ($IC_{50}$) was determined from four separate experiments: $IC_{50}$=1.3±0.5 mM (mean±standard deviation). In contrast, the corresponding end-capped peptide disulphide-cyclo-[Ac-Cys-Glu-Gln-Tyr-Cys-$NH_2$], disclosed previously in PCT/GB94/01315, was without any effect in the same assay up to the highest concentration tested (1.5 mM). Unlike the peptide containing free termini, which is freely soluble in physiological media, the latter end-capped peptide cannot be tested at concentrations above ca. 1.5 mM, due to poor solubility properties.

EXAMPLE 4

Effect of disulphide-cyclo-[H-Cys-Glu-Gln-Tyr-Cys-OH] on tissue factor-dependent human arterial thrombogenesis The efficacy of peptides was tested in a human ex vivo model of TF-dependent arterial thrombogenesis, essentially as described (K. S. Sakariassen et al., 1990, Arteriosclerosis, 10, 276; U. Ørvim et al., 1995, Arterioscl. Thromb. Vasc. Biol., in press). Human non-anticoagulated blood was drawn directly from an antecubital vein and mixed with peptide solution in a heparin-coated mixing device situated proximally to a perfusion chamber which contained a TF-coated coverslip (Thromborel S®). Blood flow was kept at 10 mL/min for 4 minutes, producing a shear rate of 650 $s^{-1}$, typical for small arteries.

Using this assay, six experiments were performed with the peptide disulphide-cyclo-[H-Cys-Glu-Gln-Tyr-Cys-OH] at five different final plasma concentrations. The peptide affected all four parameters characterising thrombus formation (platelet/fibrin adhesion, platelet/thrombus volume, fibrin deposition and thrombin activation) in a dose-dependent manner with an overall half-maximal inhibition value of 0.5 mM. A negative control peptide with unrelated sequence (H-Tyr-Ala-Asp-Lys-Ile-Glu-Asp-Thr-Lys-Leu-OH) had no effect on thrombus formation at 1 mM plasma concentration. The results are summarised in FIG. 2 (Legend: A) platelet-fibrin adhesion; B) surface coverage with fibrin; C) thrombus volume; D) thrombin-antithrombin formation) in which the results are expressed as percentages of control values obtained by infusion of saline alone.

---

---

We claim:

1. Disulphide-cyclo-[H-Cys-Glu-Gln-Tyr-Cys-OH] or a pharmaceutically acceptable salt salts thereof.

2. A pharmaceutical composition comprising disulphide-cyclo-[H-Cys-Glu-Gln-Tyr-Cys-OH] or a pharmaceutically acceptable salt thereof.

3. A pharmaceutical composition as claimed in claim 2 in a form suitable for nasal, oral, rectal or parenteral administration.

4. A method of treatment of blood disorders in the mammalian body comprising administering an effective amount of disulphide-cyclo-[H-Cys-Glu-Gln-Tyr-Cys-OH] or a pharmaceutically acceptable salt thereof to said body.

5. A method of prophylaxis comprising administering to a patient an effective amount of disulphide-cyclo-[H-Cys-Glu-Gln-Tyr-Cys-OH] or a pharmaceutically acceptable salt thereof to prevent or reduce the occurrence of blood clotting problems.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 5 amino acids
      (B) TYPE: amino acid
      (C) STRANDEDNESS: single
      (D) TOPOLOGY: cyclic (ii) MOLECULE TYPE: peptide (xi) SEQUENCE DESCRIPTION: SEQ ID NO: 1:

Cys Glu Gln Tyr Cys
1             5